United States Patent [19]

Chu et al.

[11] 4,264,590
[45] Apr. 28, 1981

[54] ANTIBACTERIAL PEPTIDE

[75] Inventors: Daniel T. Chu, Lake Villa; Jerry R. Martin, Waukegan; Alford M. Thomas, Wadsworth; Norman E. Wideburg, Waukegan, all of Ill.

[73] Assignee: Abbott Laboratories, North Chicago, Ill.

[21] Appl. No.: 157,617

[22] Filed: Jun. 9, 1980

Related U.S. Application Data

[63] Continuation-in-part of Ser. No. 41,679, May 23, 1979, abandoned, which is a continuation-in-part of Ser. No. 953,516, Oct. 23, 1978, abandoned.

[51] Int. Cl.$^3$ .................. A61K 37/00; C07C 103/52
[52] U.S. Cl. .......................... 424/177; 260/112.5 R; 424/319; 562/574
[58] Field of Search ............. 260/112.5 R, 112.5 LH, 260/112.5 TR, 112.5 S; 424/177, 319; 562/574

[56] References Cited

U.S. PATENT DOCUMENTS

| | | | |
|---|---|---|---|
| 3,956,367 | 5/1976 | Kollonitch | 562/574 |
| 4,028,405 | 6/1977 | Kollonitch et al. | 562/574 |
| 4,048,224 | 9/1977 | Chemerda et al. | 562/574 |

Primary Examiner—Delbert R. Phillips
Assistant Examiner—Blondel Hazel
Attorney, Agent, or Firm—Paul D. Burgauer; Robert L. Niblack

[57] ABSTRACT

It has been found that dipeptides containing a 3-halo-D-alanine C-terminus are powerful antibacterials and produce a highly useful synergistic effect with antibiotics.

19 Claims, No Drawings

ANTIBACTERIAL PEPTIDE

BACKGROUND OF THE INVENTION

This application is a continuation-in-part of U.S. Ser. No. 041,679 filed May 23, 1979 now abandoned which in turn was a c-i-p of U.S. Ser. No. 953,516, filed Oct. 23, 1978, now abandoned.

DETAILED DESCRIPTION OF THE INVENTION

As micro-organisms become resistant to known antibiotics, continued effort is needed to find new compounds or combinations of compounds which effectively inhibit bacteria growth.

It has now been found that a peptide of the formula

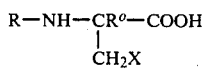

wherein the shown aminoacid is in the D-configuration, X is chlorine or fluorine, and R is the acyl moiety of a naturally occurring α-amino acid in the L-configuration, or an α-amino fatty acid, wherein the α-amino group may carry a fatty acid acyl group or an aminoloweralkyl acyl group or a loweralkyl group, $R^o$ is hydrogen or deuterium, or the corresponding loweralkyl esters of said dipeptide, or nontoxic acid addition salts thereof, are useful antibacterials; they also represent powerful synergists for D-cycloserine and other antibiotics.

The above moiety R particularly represents the known, protein-derived aminoacids, including glycine which, of course, does not have a chiral center. The definition also includes other aminoacids where the amino group is attached to the 2- or α-position of the acid. The amino group of substituent R may also carry an acyl group of a lower fatty acid or a loweralkyl group, primarily methyl, propyl, tert. butyl, acetyl, propionyl isobutyryl and the like. The protein-derived aminoacid may be represented by leucine, valine, norvaline, proline, serine, tyrosine, alanine, phenylalanine, threonine, methionine, glutamine, histidine, arginine, lysine and tryptophane. The new dipeptides have the unnatural sequence of an L-aminoacid (or glycine) coupled to (deuterated) D-haloalanine. Such an L-D sequence is usually restricted to the cell wall components of micro-organisms, and its antibacterial activity is completely unexpected.

The new dipeptide can easily be synthesized by coupling the known β-fluoro- (or chloro-)-D-alanine with an active ester of a $N^\alpha$-protected glycine or an aminoacid in the L-configuration or a $N^\alpha$-alkyl homolog thereof. Among the active esters, the hydroxysuccinimide, pentachlorophenyl, 4-nitrophenyl, 2,4,5-trichlorophenyl, a fluorophenyl, N-hydroxyisobornyldicarboximide or similarly familiar esters of RCOO— can be used for the coupling reaction. The $N^\alpha$- group and any other sensitive functional group in the aminoacid moiety represented by R above can be protected with the usual well-known groups that can subsequently be removed by a mild chemical reaction which does not affect the peptide bond formed. Among the groups frequently used as temporary protection are the carbobenzoxy (hereinafter identified as Z) or the tert. butoxycarbonyl for amino groups, particularly the $N^\alpha$-group, while benzyl or other moieties can be used to protect the hydroxy groups in serine, tyrosine or hydroxyproline or the imidazol group of histidine. Hydrogenation will remove said benzyl group after the peptide coupling has been effected and treatment with hydrobromic acid or hydrofluoric acid will remove other protective groups used by the skilled artisan, without cleaving the peptide bond. The free acid can be converted into the desired alkyl ester in known fashion and/or the $N^\alpha$- group can be acylated in known manner. The identical sequence can also be used when the starting material is the 2-deuterated 3-halo-D-alanine.

In order to illlustrate the preparation of the new peptides, reference is made to the following examples which, however, are not intended to limit this invention in any respect. In all examples, the optical rotations were taken at 25° C. in 1 N HCl at the concentrations given.

EXAMPLE 1

(a) To a stirred solution of 214.2 mg. of β-fluoro-D-alanine and 420 mg. of sodium bicarbonate in 5 ml. of water was added a solution of 800.8 mg. of carbobenzoxy-L-alanine N-hydroxysuccinimide ester in 5 ml. of 1,2-dimethoxyethane. After stirring overnight at ambient temperature, the solution was concentrated to a syrup under reduced pressure. The residue was dissolved in 10 ml. of water and acidified with 1 N-hydrochloric acid to precipitate 521 mg. of N-carbobenzoxy-L-alanyl-β-fluoro-D-alanine, m.p. 156°-7° C.

(b) A solution of 2.48 g. of this protected dipeptide in 10 ml. of 32% hydrobromic acid in acetic acid was stirred at room temperature for 30 minutes. A gummy solid was precipitated by the addition of ether. This material was washed with 3 portions of ether by decantation and crystallized from wet acetic acid, producing 1.44 g. of L-alanyl-β-fluoro-D-alanine hydrobromide, m.p. 203°-5° C. (with decomposition); $[\alpha]_D +25.3°$ (c, 1.1).

EXAMPLE 2

(a) By repeating the process of Example 1(a), but starting with 320 mg. of β-chloro-D-alanine hydrochloride and 588 mg. of sodium carbonate, 647 mg. of N-carbobenzoxy-L-alanyl-β-chloro-D-alanine was obtained; m.p. 168°-70° C.

(b) A solution of 736 mg. of this protected peptide in 101 ml. of methanol containing one equivalent of HCl was hydrogenated over 0.15 g. of 5% Pd on carbon. The catalyst was removed by filtration after the calculated amount of gaseous hydrogen had been absorbed. The catalyst was washed with methanol which was combined with the filtrate. This mixture was evaporated to dryness and the residue was placed on a 1.5×40 cm. column charged with a strongly basic polystyrene ion exchange resin and eluted with 0.1 molar ammonium acetate buffer of pH 7.5. The appropriate fractions were combined to produce a solid which was crystallized from water/acetonitrile and then from water/isopropanol to give 267 mg. of L-alanyl-β-chloro-D-alanine; m.p. 196°-202° C. (with decomposition); $[\alpha]_D +1°$ (c, 1.0).

EXAMPLES 3-14

In like manner, the compounds shown in Table I were made, identified by the melting point of the $N^\alpha$-Z-dipeptide, and the m.p. and/or optical rotation (shown as $[\alpha]_D$/concentration in 1 N HCl) of the dipeptide with the The mentioned intermediate showed a m.p. of 169°–70° C.; $[\alpha]_D+66°$ (c, 0.5).

TABLE I

| Example | Cpmpound | m.p. of Z-Dpipetide | m.p. of Dipeptide | $[\alpha]_D^{25}$/Concentration |
|---------|----------|---------------------|-------------------|---------------------------------|
| 3 | L-Val-βF-D-Ala | 198–210° | >275° d | +61.7°/1.0 |
| 4 | L-Leu-βF-D-Ala | 148–50° | >275° d | +47.0°/0.9 |
| 5 | L-Phe-βF-D-Ala |  | 240° d | +12.6°/1.0 |
| 6 | L-Lys-βF-D-Ala |  | 210° s | +27.8°/1.0 |
| 7 | L-Pro-βF-D-Ala | 130–3° | 195–7° d | −25.2°/1.0 |
| 8 | L-Ser-βF-D-Ala | 85° | 175–80° d | +21°/1.0 |
| 9 | L-Glu-βF-D-Ala |  | 120° d | +23.4°/1.0 |
| 10 | Gly-βF-D-Ala | 151–2° | 137.5–9° d | +115°/0.4 |
| 11 | Sar-βF-D-Ala | 150° d | 169–70.5° | +13.6°/0.6 |
| 12 | Gly-βCl-D-Ala | 136–6.5° | 129.5–31° d | +13.5°/0.5 |
| 13 | L-Leu-βCl-D-Ala | 137–9° | 168–9° d | −5°/0.2 |
| 14 | L-Val-βCl-D-Ala | 170–72° | 169–70° d | +19.4°/0.7 | chemical formula of the compound. All degrees (°) are in Centigrade; "d" and "s" are used to show that the compound decomposed or sintered at or before melting.

Where no optical identification is given for the N-terminal aminoacid in the above table or in the following examples, a racemic mixture was used.

EXAMPLE 15

In an ice bath, 1.07 g. of β-fluoro-D-alanine in 20 ml. of methanol was treated with 1.1 ml. of $SOCl_2$. The mixture was stirred two days at room temperature to give a clear solution. Solvent evaporation and trituration with ether gave 1.28 g. of the methyl ester of βF-D-Ala which melts at 130° C. with previous sintering above 110° C.

A 630 mg. sample of this ester was treated as in Example 1(a), producing 738 mg. of amorphous Z-L-Ala-βF-D-Ala-OMe.

A 620 mg. sample of the above $N^\alpha$-protected dipeptide ester was hydrogenated in the presence of 0.1 g. 5% Pd, 2 millimoles of hydrochloric acid and 100 ml. of methanol. Evaporation of the solvent followed by ether trituration and extensive drying gave an extemely hygroscopic gum of L-Ala-βF-D-Ala-OMe.HCl; $[\alpha]_D+41°$ (c, 1.10).

In analogy to the above procedure, the corresponding ethyl or butyl esters are made by replacing the above methanol with ethanol or butanol.

EXAMPLE 16

(a) A suspension of 512 mg. of the compound of Example 1 in 10 ml. of DMF was stirred with 1.0 ml. of acetic anhydride. After 90 minutes, the clear solution was diluted with water, evaporated to dryness and the residue placed on a chromatographic column containing AG-1-X2 (OAc), (an anionic exchange resin sold by the Dow Chemical Co.). Elution with 0.05 molar ammonium acetate gave 475 mg. of the ammonium salt of $N^\alpha$-Ac-L-Ala; $[\alpha]_D-21.2°$ (c, 1.3).

(b) Acylation with $N^\alpha$-Z-L-Ala-ONSu followed by hydrogenation as in Example 2 afforded the tripeptide L-Ala-L-Ala-βF-D-Ala; m.p. 267°–70° C. (d).

In the same fashion, $N^\alpha$-propionyl, $N^\alpha$-glycyl, $N^\alpha$-valyl, $N^\alpha$-leucyl, and $N^\alpha$-butyryl dipeptides are prepared.

EXAMPLE 17

In analogy with Example 1, the $N^\alpha$-carbobenzoxy derivative of L-α-aminobutyric acid was coupled to βF-D-Ala, followed by the usual deprotection reaction to give L-αNH₂-But-βF-D-Ala melting at 182° C.(d).

EXAMPLE 18

Using βCl-D-Ala in the procedure of Example 17 gave a $N^\alpha$-protected intermediate melting at 166°–8° C. The dipeptide L-αNH₂-But-βCl-D-Ala melts at 171.5°–2.5° C.; $[\alpha]_D+17.1°$ (c, 0.5).

EXAMPLE 19

In a manner suitable to Example 1(a), $N^\alpha$-tertbutyloxycarbonyl-L-novaline was coupled to βF-D-Ala to yield the t-BOC-L-norvalyl-βF-D-Ala. It was then deprotected as follows:

A solution of 550 mg. of the above dipeptide in 5 ml. tetrahydrofuran was added to 5 ml. 2 N hydrochloric acid. It was evaporated under reduced pressure to dryness after being stirred at room temperature for 17 hours. The residue was dissolved in 10 ml. ethanol. 2 m. of propylene oxide was added. After stirring in cold room for 24 hours, it was filtered yielding 250 mg. L-Norval-βF-D-Ala. Recrystallization from water gave pure dipeptide; m.p. 207° C. (d); $[\alpha]_D+52°$ (c, 0.5).

EXAMPLE 20

A suspension of 2.34 g. of D,L-α-amino-octanoic acid in 30 ml. of water containing 2.52 g. of $NaHCO_3$ was stirred in an ice bath with a solution of 4.38 g. of carbobenzoxy-N-hydroxysuccinimidyl carbonate in 30 ml. of 1,2-dimethoxyethane. After 3 hours, the temperature was allowed to adjust to room temperature and stirring was continued for three days. The resulting solution was cooled in an ice bath and acidified with 2NH6 to produce 2.1 g. of the desired protected amino acid; m.p. 89°–92° C.

The active N-hydroxysuccinimide ester of the above was made in known fashion; it melts at 90°–5° C. This material was coupled to βF-D-Ala in the fashion shown in the preceding examples. The $N^\alpha$-protected dipeptide melts at 116°–22° C., while the desired D,L-α-amino-octanoyl-βF-D-Ala melts at 185°–92° C.; $[\alpha]_D+19°$ (c, 0.5).

EXAMPLE 21

In analogy to Example 1(a), 432 mg. of βF-D-Ala-2-d (made according to Dolling et al., J. Org. Chem., 43 1634 of 1978) was reacted in 840 mg. of $NaHCO_3$ in 10 ml. water with 1.81 g. N-carbobenzoxy-L-leucine N-hydroxysuccinimide ester in 15 ml. of 1,2-dimethoxyethane. After acidification and refrigeration for 24 hrs., amorphous $N^\alpha$-Z-L-Leu-βF-D-Ala-2-d was obtained which was washed with water. The solid was hydrogenolized in 100 ml. of methanol at 3 atm. $H_2$ pressure in the presence of 0.3 g. of 5% Pd-on-carbon, followed by filtration. The filtrate was evaporated and the solid was washed with ethyl ether and dried to produce L-Leu-βF-D-Ala-2-d; $[\alpha]_D^{25}$ 28.6° (c, 1).

The corresponding chloro-analog is made in the same fashion, although the yield of βCl-D-Ala-2-d using the method of Dolling et al. is appreciably lower than for the βF-intermediate.

Other compounds of the above general description can easily be made by repeating Example 1(a) or 21 but using the succinimide esters of other $N^\alpha$-protected amino acids. For instance, if said ester is that of isoleucine or α-aminocaproic acid, the corresponding compounds are obtained where R represents L-isoleucyl or L-α-aminoaminocaproyl. Obviously, other amino acid esters carrying protected additional functional groups can be employed to make the dipeptides of the current invention. Particularly, the L-threonyl-, L-tryptophyl- and L-tyrosyl-β-fluoro-(or chloro)-D-alanines or -D-alanines-2-d can be made by the above route. In all cases, the functional groups, where present, can be temporarily protected in known fashion by benzyl, carbobenzyloxy, tert. butyl or other protective groups commonly used in the peptide art.

In order to show the pronounced synergistic activity of the new compounds with D-cycloserine, reference is made to the following in vitro tests.

In a two-fold agar dilution assay with *E. coli* (Juhl) and *E. coli* 6880 as test organisms, compounds of Examples 1 and 2 show a minimum inhibitory concentration (M.I.C.) of >800 ppm. D-cycloserine alone shows a M.I.C. of 12.5 ppm against the former and 6.2 ppm against the latter *E. coli* strain. The combination of the new peptide with D-cycloserine produces the following M.I.C. test results.

| Example | Combination Ratio | *E. coli* (Juhl) M.I.C. | *E. coli* 6880 M.I.C. |
|---|---|---|---|
|  | 1:8 | 0.2:1.56 | 0.1:0.78 |
| 1 | 1:1 | 0.2:0.2 | 0.1:0.1 |
|  | 8:1 | 0.39:0.05 | 0.39:0.05 |
|  | 1:8 | 0.2:1.56 | 0.1:0.78 |
| 2 | 1:1 | 0.78:0.78 | 0.78:0.78 |
|  | 8:1 | 0.62:0.78 | 3.1:0.39 |

As shown, the compounds of the current invention allow the use of much lower concentrations of both compounds to get the desired antibacterial results.

The in vitro activity of the halogenated peptides and the halogenated peptide-antibiotic combinations provided by the present invention can be demonstrated as follows:

The halogenated peptides alone, the antibiotic alone or mixtures of the halogenated peptides and selected antibiotics are prepared in sterile concentrated aqueous solutions at the desired ratios. Serial dilutions are made to give a range of concentrations of the test substances. Samples of the dilutions are mixed with an appropriate sterile synthetic medium in test tubes. The tubes are then inoculated with an appropriate test organism and incubated at 35°–37° C. for 16–20 hours. Minimum inhibitory concentrations, i.e., that concentration which inhibits visible growth, are read and the fractional inhibitory concentration indices (F.I.C.) are calculated. The results obtained using representative halogenated peptides and representative antibiotics are given in Table II. In all instances, *E. coli* (Juhl) was used as the infecting microorganism.

TABLE II

| Ex. | Antibiotic | MIC ppm Peptide | MIC ppm Antibiotic | MIC ppm Pep/Antib. | Ratio Pep/Antib. | F.I.C. Index |
|---|---|---|---|---|---|---|
| 1 | D-cycloserine | >800 | 12.5 | 0.2/1.56 | 1:8 | 0.12 |
| 1 | D-cycloserine | >800 | 12.5 | 0.2/0.2 | 1:1 | 0.02 |
| 1 | D-cycloserine | >800 | 12.5 | 0.39/0.05 | 8:1 | 0.004 |
| 2 | D-cycloserine | >800 | 12.5 | 0.2/1.56 | 1:8 | 0.12 |
| 2 | D-cycloserine | >800 | 12.5 | 0.78/0.78 | 1:1 | 0.06 |
| 2 | cephalothin | >800 | 6.2 | 3.1/3.1 | 1:1 | 0.50 |
| 4 | carbencillin | >200 | 6.2 | 1.56/12.5 | 1:8 | 2.0 |
| 4 | carbencillin | >200 | 6.2 | 1.56/1.56 | 1:1 | 0.25 |
| 4 | D-cycloserine | >100 | 12.5 | 0.1/0.78 | 1:8 | 0.06 |
| 4 | D-cycloserine | >100 | 12.5 | 0.1/0.1 | 1:1 | 0.008 |
| 8 | D-cycloserine | >800 | 12.5 | 0.05/0.39 | 1:8 | 0.03 |
| 8 | D-cycloserine | >800 | 12.5 | 0.1/0.1 | 1:1 | 0.008 |
| 8 | D-cycloserine | >800 | 12.5 | 0.39/0.05 | 8:1 | 0.004 |
| 9 | D-cycloserine | >800 | 6.2 | 0.39/3.1 | 1:8 | 0.50 |

The in vivo activity of the halogenated peptides and the halogenated peptide-antibiotic combinations provided by the present invention can be demonstrated as follows:

Charles River mice, weighing approximately 20 g. each, are infected intraperitoneally with 10–100 times the LD of the infecting organism. At predetermined intervals post-infection, e.g., 1 and 5 hours, mice are dosed subcutaneously with graded doses of the halogenated peptide, antibiotic and combination thereof. The number of mice surviving each treatment for 7 days post-infection is observed and the $CD_{50}$ is calculated. The fractional inhibitory concentration (F.I.C.) for each combination is calculated in the usual manner. The results using D-cycloserine as an example of the antibiotic and representative halogenated peptides are shown in Table III.

In this table, the following infecting microorganisms were used:

*S. aureus* (Smith)
*E. coli* (Juhl)
*E. coli* (305-101)
*Strep. pyrogenes* (C 203).

The infecting organisms are listed by the above code; the compounds are listed by their Example number. In all instances, the dipeptide and D-cycloserine were tested at a ratio of 10:1. The $CD_{50}$ combination column lists only the amount of peptide present; the D-cycloserine amount is 10% of the listed amount.

TABLE III

| Example | Organism | $CD_{50}$(mg/kg) Peptide | $CD_{50}$(mg/kg) Cycloserine | $CD_{50}$(mg/kg) Combination | F.I.C. Index |
|---|---|---|---|---|---|
| 1 | *S. aureus* | 9.2 | 7.3 | <3.1 | <0.37 |
| 1 | *E. coli* (305–101) | 26 | 63 | 25 | 0.90 |
| 1 | *Strep. pyrogenes* | 17.8 | >100 | 10.9 | 0.60 |
| 2 | *S. aureus* | 170 | 24 | 35 | 0.34 |
| 3 | *S. aureus* | 10 | 7 | 1.0 | 0.15 |
| 4 | *S. aureus* | 7.4 | 5.4 | 1.6 | 0.25 |
| 4 | *E. coli* (Juhl) | 25.9 | 42.6 | 10.1 | 0.41 |
| 5 | *S. aureus* | 14.4 | 27 | 13.6 | 0.99 |

TABLE III-continued

| Example | Organism | CD$_{50}$(mg/kg) Peptide | CD$_{50}$(mg/kg) Cycloserine | CD$_{50}$(mg/kg) Combination | F.I.C. Index |
|---|---|---|---|---|---|
| 6 | S. aureus | 100.4 | 28.8 | 6.8 | 0.08 |
| 6 | S. aureus | 32 | 29 | 4.0 | 0.13 |
| 7 | S. aureus | 12.2 | 8.4 | 3.7 | 0.35 |
| 8 | S. aureus | 48 | 20 | 5.2 | 0.13 |
| 9 | S. aureus | 28.5 | 17.3 | 7.6 | 0.30 |
| 9 | E. coli (Juhl) | 81 | 102 | 72 | 0.96 |
| 10 | S. aureus | 19 | 19 | 4.7 | 0.27 |
| 11 | S. aureus | 29 | 19 | 6.2 | 0.24 |
| 12 | S. aureus | 155 | 9.2 | 17.4 | 0.30 |
| 15 | S. aureus | 18 | 24 | 5.5 | 0.32 |
| 16 | S. aureus | 85 | 24 | 18 | 0.28 |
| 17 | S. aureus | 13.7 | 13.7 | 2.6 | 0.20 |
| 20 | S. aureus | 75.9 | 22.5 | 8.6 | 0.10 |

The compounds of the present invention can be administered intramuscularly, orally, subcutaneously or intravenously. Sterile, liquid dosage forms can easily be prepared for parenteral administration by dissolving the above dipeptide in the form of a water-soluble, nontoxic salt in isotonic sodium chloride solutions containing optional buffers, stabilizers, and/or preservatives. Liquid oral dosage forms in the form of elixirs, syrups or suspensions can be made in standard fashion, also optionally containing the above additives together with coloring or flavoring agents.

Solid dosage forms for oral administration include tablets, capsules, pills and wafers. For these dosage forms, the usual solid diluents are used where required. Capsules can be filled with undiluted powdered or granulated crystals of the new compounds. For tablets, the following standard procedure may be used:

About one-half of 50 g. of cornstarch is milled together with 50 g. of the above dipeptide and 220 g. of calcium phosphate dibasic dihydrate. This blend is milled until homogenous and passed through a 40-mesh screen. The remaining portion of the cornstarch is granulated with water, heated and mixed with the above drug blend in a hot air oven at 50° C. and sifted through a 16-mesh screen. These granules are then mixed with 16 g. of talcum powder, 4 g. of magnesium stearate and 0.8 g. of combined coloring and flavoring additives. The mixture is blended to homogeneity, passed through a 30-mesh screen and blended for another 15 minutes. This blend is compressed into tablets weighing approximately 350 mg. using a 9/32" standard convex punch resulting in tablets of a hardness of 7-9 with each tablet containing 50 mg. of the drug. In a similar fashion, tablets weighing 600 mg. containing 250 mg. of drug can be prepared, preferably in a tableting machine producing bisected tablets.

While the above examples are directed to the peptides per se, the acid addition salts can readily be prepared in known fashion. The nontoxic salts useful as antibacterials include primarily the hydrochloride, phosphate, sulfate, acetate, succinate and citrate.

As will be seen from the above examples, the current dipeptides are antibacterially active in warm-blooded animals. Against certain bacteria, the new dipeptides are powerful synergists for known antibacterials, enabling the use of the latter in quantities of only a small fraction of its curtive dose. In particular, by combining the current dipeptide with a medicinally useful antibiotic in a weight ratio of 1:1 to 10:1, excellent antibacterial synergism is observed. While the demonstrated synergistic results above are based on the use of specific antibiotics, it will be understood that other antibiotics including penicillins other than the above carbenicillin, cephalosporins other than cephalothin, streptomycin, erythromycin, tetracyclin, etc. can be combined with the new peptides to obtain better results than with such antibiotics alone.

We claim:

1. A peptide of the formula

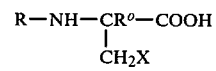

wherein the shown aminoacid is in the D-configuration, X is chlorine or fluorine, R$^o$ is hydrogen or deuterium, and R is the acyl moiety of a naturally occurring aminoacid in the L-configuration or an α-amino fatty acid wherein the α-amino group may carry a fatty acid acyl group, an aminoloweralkyl acyl group or a loweralkyl group, or the corresponding loweralkyl esters of said peptide, or nontoxic acid addition salts thereof.

2. A peptide according to claim 1 wherein R$^o$ is hydrogen.

3. The peptide of claim 2 wherein X is fluorine and R is the acyl moiety of L-serine.

4. A peptide of the formula

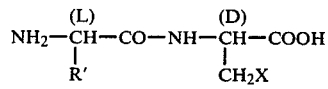

wherein X is fluorine or chlorine and R' is H or an alkyl group of 1-8 carbons, or a nontoxic acid addition salt thereof.

5. The compond of claim 4 wherein X is fluorine and R' is methyl.

6. The compound of claim 4 wherein X is fluorine and R' is isobutyl.

7. The compound of claim 4 wherein X is fluorine and R' is isopropyl.

8. The compound of claim 4 wherein X is chlorine and R' is methyl.

9. The compound of claim 4 wherein X is chlorine and R' is isobutyl.

10. An antibacterial composition containing, as the active principle, an antibacterially effective amount of a compound of formula

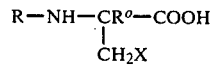

wherein the shown aminoacid is in the D-configuration, X is chlorine or fluorine, $R^o$ is hydrogen or deuterium, and R is the acyl moiety of a naturally occurring aminoacid in the L-configuration or an α-amino fatty acid wherein the α-amino group may carry a fatty acid acyl group, or an aminoloweralkyl acyl group or a loweralkyl group, or the corresponding loweralkyl esters of said peptide, or nontoxic acid addition salts thereof, together with between 0-50% by weight thereof of an antibiotic and a pharmaceutically acceptable diluent.

11. The composition of claim 10 wherein $R^o$ is hydrogen.

12. The composition of claim 10 in the form of an oral preparation.

13. The composition of claim 10 wherein said antibiotic is D-cycloserine and is present in an amount of between 12.5 and 50% by weight.

14. The composition of claim 11 wherein X is fluorine and R is the acyl moiety of L-serine.

15. An antibacterial composition containing, as the active principle, an antibacterially effective amount of a compound of the formula

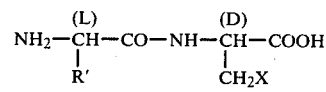

wherein X is fluorine or chlorine and R' is H or an alkyl group of 1-8 carbons, or a nontoxic acid addition salt thereof, together with 0-50% by weight thereof of an antibiotic, and a pharmaceutically acceptable diluent.

16. The composition of claim 15 wherein X is fluorine and R' is methyl.

17. The composition of claim 15 wherein X is fluorine and R' is isobutyl.

18. The composition of claim 15 wherein X is chlorine and R' is isobutyl.

19. The composition of claim 15 wherein X is chlorine and R' is methyl.

* * * * *